United States Patent [19]
Yamamoto et al.

[11] Patent Number: 5,908,766
[45] Date of Patent: *Jun. 1, 1999

[54] METHOD OF THE PRODUCTION OF SACCHARIDES CONTAINING SIALIC ACID

[75] Inventors: Takeshi Yamamoto; Motoko Nakashizuka, both of Kanagawa; Ichiro Terada, Osaka; Hisashi Kodama, Tokyo, all of Japan

[73] Assignee: Japan Tobacco Inc., Tokyo, Japan

[*] Notice: This patent is subject to a terminal disclaimer.

[21] Appl. No.: 08/741,663

[22] Filed: Oct. 31, 1996

[51] Int. Cl.$^6$ .................... C12P 19/18; C12P 19/44; C12P 19/26; C12P 19/04
[52] U.S. Cl. .................. 435/97; 435/74; 435/84; 435/100; 435/101
[58] Field of Search .................. 435/97, 74, 84, 435/100, 101

[56] References Cited

U.S. PATENT DOCUMENTS

| | | | |
|---|---|---|---|
| 4,925,796 | 5/1990 | Bergh et al. | 435/97 |
| 5,278,299 | 1/1994 | Wong et al. | 536/53 |
| 5,374,541 | 12/1994 | Wong et al. | 435/74 |

OTHER PUBLICATIONS

Yamamoto et al, J. Biochem. 120 (1): 104–110 (1996).
Derwent WPI, JP 8154673, English Abstract (Jun. 18, 1996).
Derwent WPI, JP 8173182, English Abstract (Jul. 9, 1996).
Paulson et al, The Journal of Biological Chemistry, vol. 252, No. 7, pp. 2356–2371 (1977).
Weinstein et al, The Journal of Biological Chemistry, vol. 257, No. 22, pp. 13835–13844 (1982).
Miyagi et al, Eur. J. Biochem., vol. 126, pp. 253–261 (1982).
Gross et al, Biochemistry, vol. 28, pp. 7386–7392 (1989).
Bauvois et al, Eur. J. Biochem., vol. 121, pp. 567–572 (1982).
Bendiak et al, Eur. J. Biochem., vol. 128, pp. 355–362 (1982).
Gross et al, Eur. J. Biochem., vol. 168, pp. 595–602 (1987).

*Primary Examiner*—Francisco Prats
*Attorney, Agent, or Firm*—Birch, Stewart, Kolasch & Birch, LLP

[57] ABSTRACT

Described is a method of production of saccharides containing sialic acid, wherein β-galactoside-α-2,6-sialyltransferase is used for linking sialic acid to the 6-position of a galactose residue in a sugar chain of a glycoconjugate or the 6-position of a galactose residue in a free sugar chain, or to the 6-position of a monosaccharide having a hydroxyl group on carbon at the 6-position and being capable of forming an oligosaccharide or a glycoconjugate.

7 Claims, 6 Drawing Sheets

1: Methyl-β-D-Gal
2: Methyl-α-D-Gal
3: Methyl-β-D-Man
4: Methyl-α-D-Man
5: Methyl-β-D-GlcNAc
6: Methyl-α-D-GalNAc

METHOD OF THE PRODUCTION OF SACCHARIDES CONTAINING SIALIC ACID

BACKGROUND OF THE INVENTION

Recently, the biological activities of glycoconjugates such as glycoproteins, glycolipids etc. in animal cells have been revealed and the importance of sugar chains in glycoconjugates comes to be recognized. Usually, sialic acid is existed at the nonreducing terminals of sugar chains in glycoconjugates, and sialic acid is considered to have particularly many functions where the physiological functions and biological activities of sugar chains are regarded as important. So, the synthesis of sialoside is very important to examine the (biological or physiological) effect of sialosides, such as disaccharides, oligosaccharides, sugar chains in glycoconjugates, etc.

For linking of sialic acid via an α-2,6-linkage to the 6-position of monosaccharides such as galactose, mannose, N-acetylgalactosamine and N-acetylglucosamine or to the 6-position of a galactose residue present at the nonreducing terminal of a free sugar chain derived from glycoconjugates such oligosaccharides, glycoproteins or glycolipids, chemical synthesis method and enzymatic synthesis method are known. The chemical synthesis method is flexible and nearly limitless as compared with the enzymatic synthesis method, but the procedure is complicated and side reactions also occur, so it is extremely difficult to efficiently synthesize a product having sialic acid linked selectively to the 6-position of its galactose.

On the other hand, the enzymatic synthesis method is extremely simple as compared with the chemical synthesis method and no side reactions occur, so it is possible to synthesize the desired product in high yield. Enzymes used therein are obtained from internal organs such as the submaxillary gland, liver etc. in animals such as rats, pigs, humans etc. (Poulson et al., J. Biol. Chem. 252, 2356–2362 (1977), Weinstein et al., J. Biol. Chem. 257, 13835–13844 (1982), Miyagi et al., Eur. J. Biochem. 126, 253–261 (1982)). However, it is disadvantageous that these enzyme are expensive because they cannot be obtained in large amounts due to their difficult purification.

A certain animal-derived sialyltransferase has already been cloned, but sialyltransferase has still not been supplied inexpensively in large amounts. Therefore, the synthesis of sialic acid-containing oligosaccharides or glycoconjugates is extremely difficult under these circumstances.

SUMMARY OF THE INVENTION

The object of the present invention is to provide a method of production of sialic acid-containing saccharides inexpensively in large amounts.

As a result of their eager research, the present inventors found that marine microorganisms belonging to the genus Photobacterium produce an enzyme for transferring sialic acid to a galactose residue etc. in a sugar chain of a glycoconjugate or in a free sugar chain, and also that this enzyme can be used to produce sialic acid-containing saccharides easily and inexpensively.

Specifically, the present invention is a method of production of saccharides containing sialic acid, wherein β-galactoside-α-2,6-sialyltransferase is used for linking sialic acid to the 6-position of a galactose residue in a sugar chain of a glycoconjugate or the 6-position of a galactose residue in a free sugar chain, or to the 6-position of a monosaccharide having a hydroxyl group on carbon at the 6-position and being capable of forming an oligosaccharide or glycoconjugate.

Further, the present invention is a method of production of saccharides containing sialic acid, wherein said β-galactoside-α-2,6-sialyltransferase is derived from a microorganism belonging to the genus Photobacterium and has the following physicochemical properties [a] or [b]:

[a]
(1) action and specificity: transferring sialic acid from cytidine monophosphate(CMP)-sialic acid to the 6-position of a galactose residue in a sugar chain of a glycoconjugate or in a free sugar chain, or to the 6-position of a monosaccharide having a hydroxyl group on carbon at the 6-position and being capable of forming an oligosaccharide or a glycoconjugate;
(2) optimum pH: 5 to 6;
(3) optimum temperature: 30° C.; and
(4) molecular weight: 64,000±5,000 (determined by gel filtration).

[b]
(1) action and specificity: transferring sialic acid from cytidine monophosphate-sialic acid to the 6-position of a galactose residue in a sugar chain of a glycoconjugate or in a free sugar chain, or to the 6-position of a monosaccharide having a hydroxyl group on carbon at the 6-position and being capable of forming an oligosaccharide or a glycoconjugate;
(2) optimum pH: 5;
(3) optimum temperature: 30° C.;
(4) pH stability: 4.5 to 6;
(5) thermal stability: keeping about 90% of the initial activity after heating at 35° C. for 5 minutes and about 70% of the initial activity after heating at 45° C. for 5 minutes;
(6) molecular weight: about 61,000 (determined by 12.5% SDS-polyacrylamide gel electrophoresis) and about 64,000 (determined by gel filtration);
(7) N-terminal amino acid sequence:
X-Asn-Ser-Asp-Asn-Thr-Ser-Leu-Lys-Glu-Thr-Val (SEQ ID NO:1); and
(8) isoelectric point: 4.6.

DESCRIPTION OF THE PREFERRED EMBODIMENT

Hereinafter, the present invention is described in detail.

The present invention relates to a method of production of sialic acid-containing saccharides and particularly to a method of production of a glycoconjugate and a free oligosaccharide containing sialic acid at the 6-position of its galactose residue, as well as a disaccharide containing sialic acid linked to the 6-position of a monosaccharide having a hydroxyl group on carbon at the 6-position and being capable of forming an oligosaccharide or a glycoconjugate containing sialic-acid.

The β-galactoside-α-2,6-sialyltransferase used in the present invention can be obtained by culturing a microorganism belonging to the genus Photobacterium capable of producing β-galactoside-α-2,6-sialyltransferase in a cell, and then recovering the resulting enzyme from the microorganism.

The microorganism used herein may be any microorganism belonging to the genus Photobacterium and having the ability to produce β-galactoside-α-2,6-sialyltransferase. Preferable microorganisms are those belonging to the species *Photobacterium damsela*. Examples are *Photobacterium damsela* JTO160, ATCC 33539, and ATCC 35083. Every *Photobacterium damsela* is a marine microorganism, and *Photobacterium damsela* JTO160 was separated from seawater in Sagami Bay, Japan. By way of example, a method of screening *Photobacterium damsela* JTO160 is shown below.

As a source of the microorganism, seawater, sea sand or sea sludge is plated directly or after dilution with sterilized seawater onto a plate medium, Marine Broth 2216-agar medium (1.5% agar, manufactured by Difco) and the marine microorganisms are grown. The microorganisms are subjected to single colony isolation in a usual manner and then the microorganism in each colony is cultured in a liquid medium, Marine Broth 2216 medium (Difco). After the microorganisms are grown sufficiently, they are harvested from the culture by centrifugation and then suspended in 20 mM cacodylate buffer (pH 6.0) containing 0.2% Triton X-100 (Kanto Kagaku K.K.) as surfactant. This suspension is subjected to ultrasonication under cooling on ice whereby the bacterial cells are disrupted. The solution of the disrupted cells is examined in a usual manner for sialyltransferase activity, and a strain with sialyltransferase activity is obtained as the microorganism of the invention.

The bacteriological properties of *Photobacterium damsela* JTO160 thus obtained are as follows:

1) Morphological features

| | |
|---|---|
| (1) Form | Bacillus, 1 × 0.5 μm to 2 × 1 μm in size |
| (2) Motility | present with flagella |
| (3) Gram stainability | negative |
| (4) Spore formation | absent |

2) Physiological properties

| | |
|---|---|
| (1) growth temperature | 25 to 35° C. |
| (2) colony color | not producing any characteristic colony color |
| (3) O-F test | F |

-continued

| | |
|---|---|
| (4) catalase test | positive |
| (5) oxidase test | positive |
| (6) formation of gas from glucose | positive |
| (7) V-P reaction | positive |
| (8) gelatin degradability | absent |
| (9) starch degradability | absent |
| (10) nitrate reducibility | present |
| (11) fluorescence | absent |
| (12) attitude toward oxygen | anaerobic |
| (13) accumulation of glucose | present |
| (14) accumulation of β-hydroxybutyric acid | absent |
| (15) utilization of β-hydroxybutyric acid | present |
| (16) requirement for Na$^+$ | present |
| (17) sensitivity to a pteridine derivative | |
|     10 μg | present |
|     150 μg | present |
| (18) quinone system | Q-8, Q-7 |
| (19) GC content in bacterial DNA (mol %)* | 42 |
| (20) lipase activity | present |
| (21) argininedihydorase activity | present |
| (22) assimilability | |
|     acetate | absent |
|     maltose | present |
|     L-proline | present |
|     pyruvate | absent |
|     D-xylose | absent |
|     cellobiose | absent |
|     D-galactose | present |
|     D-galacturonic acid | absent |
|     D-gluconate | absent |
|     glucose | present |
|     L-glutamate | absent |
|     D-mannose | present |
|     sucrose | absent |
|     mannitol | absent |

Note) *: Determined in HPLC.

From the above bacteriological properties, it was estimated that this microorganism is *Photobacterium damsela*, and finally this microorganism was identified as *Photobacterium damsela* due to its high homology (89%) in a DNA-DNA hybridization test with *Photobacterium damsela* GIFU 10450 (standard strain). This DNA-DNA hybridization test was carried out using a photobiotin label in a microplate.

*Photobacterium damsela* JTO160 was deposited as FERM BP-4900 under the conditions of the Budapest Treaty on Nov. 24, 1994 with the National Institute of Bioscience and Human-Technology, Agency of Industrial Science and Technology, Japan. *Photobacterium damsela* ATCC 33539 deposited as FERM BP-6135 and ATCC 35083 deposited as FERM BP-6136 both have been deposited with American Type Culture Collection (ATCC) under the conditions of the Budapest Treaty and the bacteriological properties of ATCC 33539 are described in Int. J. Syst. Bact.32, 267 (1982) and by MacDonell et al. in Syst. Appl. Microbiol. 6, 171–182 (1985), and the bacteriological properties of ATCC 35083 are described by Grimes et al. in Microb. Ecol.10, 271–282 (1984).

The medium used for culture of the above microorganism is a medium containing a carbon source, a nitrogen source, inorganic matter etc. which can be utilized by the microorganism. The carbon source includes peptone, triptone, casein lysate, meat extract etc., preferably peptone. The nitrogen source is preferably yeast extract. The salt used is preferably a suitable combination of sodium chloride, iron citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate, hydrogen disodium phosphate, etc.

Marine Broth 2216 (Difco), that is, a medium containing all of the above ingredients, can also be used. Further, a medium prepared by adding peptone, yeast extract etc. to artificial seawater containing suitable salts may also be used.

The culture conditions are varied more or less depending on the composition of medium. Usually, the culture temperature ranges from 15 to 35° C., preferably 20 to 33° C., the pH ranges from pH 6.8 to 8.8, preferably pH 7.3 to 8.2, and the period of culture ranges from 8 to 48 hours, preferably 16 to 24 hours.

Before separation and isolation of the enzyme, the microorganism should be disrupted in a usual manner, for example by ultrasonication, French press, glass beads, dynomill, because the desired enzyme is present in cells. Ultrasonication is used in a preferred embodiment. After insolubles are removed from the disrupted microorganism, the enzyme can be purified from the supernatant, for example by column chromatography with a suitable combination of commercial cation and anion exchange columns, gel filtration column, hydroxyapatite column, CDP-hexanolamine agarose column, CMP-hexanolamine agarose column and hydrophobic column, as well as native-polyacrylamide gel electrophoresis, etc.

β-galactoside-α-2,6-sialyltransferase may be purified completely, but because the partially purified enzyme has enough activity, both completely purified and partially purified β-galactoside-α-2,6-sialyltransferase can be used in the present invention.

The β-galactoside-α-2,6-sialyltransferase used in the present invention is characterized in that the enzyme is derived from microorganisms belonging to the genus Photobacterium, particularly microorganisms belonging to the species Photobacterium damsela and it has the action and substrate specificity of transferring sialic acid from CMP-sialic acid to the 6-position of a galactose residue in a sugar chain of a glycoconjugate or in a free sugar chain, preferably the 6-position of a galactose residue present in their nonreducing terminals, or to the 6-position of a monosaccharide having a hydroxyl group on carbon at the 6-position and being capable of forming an oligosaccharide or a glycoconjugate. The optimum pH of the present enzyme is in the range of pH 5 to 6, the optimum temperature is 30° C., and the molecular weight by gel filtration is 64,000±5,000. The glycoconjugate or free sugar chain carrying such a galactose residue may be any saccharides composed of galactose residues, regardless of whether the glycoconjugate and free sugar chain are derived from animals or plants. Examples are disaccharides, free sugar chains (derived from glycoconjugates), glycoproteins, and glycolipids. The disaccharides include lactose, N-acetyllactosamine etc.; the free sugar chains from glycoconjugates (e.g. free sugar chains composed of galactose residues, derived from glycoconjugates) include an N-acetyllactosamine type such as biantennary sugar chains etc. and N-acetyllactosamine type monosialylated such as oligosaccharides etc.; the glycoproteins include asialofetuin, asialo-$\alpha_1$-acid glycoproteins etc.; and the glycolipids include lactosylceramide and ganglioside saccharides.

The monosaccharide having a hydroxyl group on carbon at the 6-position and being capable of forming an oligosaccharide may be any monosaccharide having a pyranose-type ring containing a primary hydroxyl group at the nonreducing terminal. Examples are monosaccharides such as glucose, galactose, mannose, allose, talose etc. having a primary hydroxyl group at their reducing terminal, monosaccharides such as 3-O-methylglucopyranose, 3-O-methylgalactopyranose etc. having a substituent group at their alcoholic OH group, and monosaccharides such as methyl-galactopyranoside, ethyl-glucopyranoside etc. having a substituent group at their glycosidic hydroxy group.

Specifically, such enzyme includes the enzyme derived from Photobacterium damsela JTO160, Photobacterium damsela ATCC 33539 and Photobacterium damsela ATCC 35083. By way of example, the enzyme derived from Photobacterium damsela JTO160 has the following enzyme properties and physicochemical properties:

(1) Action and substrate specificity

The enzyme transfers sialic acid from CMP-sialic acid to the 6 position of a galactose residue in a sugar chain of a glycoconjugate or in a free sugar chain, particularly the 6-position of galactose present in its nonreducing terminal, or to the 6-position of galactose present in an oligosaccharide such as lactose, N-acetyllactosamine etc., particularly the 6-position of galactose present in its nonreducing terminal, or to the 6-position of a monosaccharide having a hydroxyl group on carbon at the 6-position and being capable of forming an oligosaccharide such as galactose, mannose, N-acetylglucosamine, N-acetylgalactosamine etc.

(2) Thermal stability

10 μl solution of the enzyme was heated for 5 minutes in a water bath at 30° C., 35° C., 40° C., 45° C., 50° C., 55° C. and 60° C., respectively, and then each enzyme solution was examined for enzyme activity. The remaining activity was determined by comparison with the activity (as 100%) of the enzyme solution which was not heated. The result indicated that the enzyme had 100% of the initial activity at 30° C., about 90% at 35° C., and about 70% at 45° C.

(3) pH stability

The enzyme was dissolved in acetate buffer (pH 3.7 to 5.0), cacodylate buffer (pH 5.0 to 7.3) and Tris-HCl buffer (pH 7.3 to 8.0), respectively, and 10 μl of each enzyme solution was examined for enzyme activity. The result indicated that the enzyme was stable in the range of pH 4.5 to 6.

(4) Optimum temperature

The optimum temperature is in the range of 30° C. to 35° C. in which the enzyme is inactivated only at a minimum level and the enzyme reaction proceeds rapidly.

(5) Optimum pH

An acceptor substrate was dissolved in acetate buffer (pH 3.7 to 5.0), cacodylate buffer (pH 5.0 to 7.3) and Tris-HCl buffer (pH 7.3 to 8.0), respectively, and the enzyme was added thereto and examined for enzyme activity. The result indicated that the optimum pH of the enzyme was pH 5.

(6) Molecular weight

The molecular weight of the enzyme was determined by SDS-polyacrylamide gel electrophoresis (SDS-PAGE) and gel filtration. In SDS-PAGE, the enzyme and a molecular marker (phosphorylase b with a molecular weight of 97,400; bovine serum albumin, 66,267; aldolase, 42,400; carbonic anhydrase, 30,000; trypsin inhibitor, 20,100; and lysozyme, 14,400) were electrophoresed in a usual manner on 12.5% polyacrylamide gel containing SDS, and the molecular weight was determined from its mobility. The result indicated that the molecular weight of the enzyme was about 61,000 (SDS-PAGE).

In gel filtration, a calibration curve was prepared by passing a molecular weight marker (aldolase with a molecular weight of 158,000; albumin, 68,000; and albumin, 45,000) through a gel filtration column AsahiPak GS-510

(Asahi Kagaku K.K.) in 20 mM phosphate buffer (pH 6.0) containing 0.2M NaCl. Then, the enzyme was passed through the column, and the molecular weight was determined on the basis of its elution position in the calibration curve. The result indicated that the molecular weight of the enzyme was about 64,000 (gel filtration).

(7) N-terminal amino acid sequence

The N-terminal amino acid sequence of the present enzyme was determined by the Edman degradation method. 20 μl solution of the enzyme (0.3 μg/μl) was subjected to SDS-PAGE (7.5% gel) in a usual manner, and the enzyme was transferred by Western blotting onto Biodaine A (Japan Paul K.K.) and its N-terminal amino acid sequence (12 amino acids from the N-terminal) was determined in Amino Acid Sequence Analyzer 477A and 120A Protein Sequencer (Applied Biosystems). The result indicated that the N-terminal amino acid sequence of the enzyme was X-Asn-Ser-Asp-Asn-Thr-Ser-Leu-Lys-Glu-Thr-Val (SEQ ID NO:1).

(8) Isoelectric point

The isoelectric point of the present enzyme was determined by isoelectric focusing in IEF 4.6-6 gel in Fast System (Pharmacia) and comparison of its mobility with that of an isoelectric marker.

In the present invention, the above-described β-galactoside-α-2,6-sialyltransferase is used to transfer sialic acid to the 6position of a monosaccharide or the 6-position of galactose present in oligosaccharides, glycoprotein sugar chains, etc., to give saccharides containing sialic acid.

Specifically, monosaccharides capable of forming oligosaccharides such as galactose, mannose, N-acetylglucosamine, N-acetylgalactosamine, etc., disaccharides such as galactose-containing lactose, N-acetyllactosamine etc., free sugar chains (derived from glycoconjugates) containing galactose, i.e. oligosaccharides such as N-acetyllactosamine type: biantennary sugar chain, N-acetyllactosamine type monosialylated: biantennary sugar chain, etc., or glycoconjugates containing galactose in their sugar moiety, i.e. glycoproteins such as asialofetuin, asialo-α$_1$-acid glycoproteins etc., and glycolipids such as lactosylceramide, gangliosides etc., are used as acceptor substrates respectively, together with CMP-sialic acid i.e. a donor substrate, and their corresponding sialo-derivatives can be produced by the action of the β-galactoside-α-2,6-sialyltransferase of the present invention. The β-galactoside-α-2,6-sialyltransferase used may be purified completely or partially.

The reaction conditions are not limited insofar as the enzyme is not inactivated. Specifically, the reaction temperature ranges from 15 to 50° C., preferably 25 to 35° C., and the reaction pH ranges from pH 4 to 7.5, preferably pH 5 to 6. Any buffer in this pH range can be used. Examples are cacodylate buffer, phosphate buffer, acetate buffer, etc.

In cases where the acceptor substrate used is monosaccharides, disaccharides such as galactose-containing lactose, N-acetyllactosamine etc., free sugar chains (derived from glycoconjugates) containing galactose, i.e. oligosaccharides such as N-acetyllactosamine type: biantennary sugar chain, N-acetyllactosamine type monosialylated: biantennary sugar chain, etc., or glycoconjugates containing galactose in their sugar moiety, i.e. glycoproteins such as asialofetuin, asialo-α$_1$-acid glycoproteins etc., reaction is initiated by adding CMP-sialic acid as a donor substrate and the completely or partially purified enzyme to such acceptor substrate in various concentrations. In this reaction, both the acceptor substrate and donor substrate are contained preferably at a 5-fold or 10-fold or more concentration than Km value (Michaelis constant).

After the reaction, the resulting reaction product (sialo-derivative corresponding to the saccharide-accepting substrate) can be isolated and purified by column chromatography.

In cases where hydrophobic glycolipids are used as the acceptor substrate, a surfactant etc. can be added to the reaction solution so that they can be mixed with the enzyme for efficient reaction. The surfactant used is non-ionic surfactant, anionic surfactant, cationic surfactant, ampholytic surfactant etc. Examples are Triton X-100, sodium dodecylsulfate, dodecylpyridinium bromide, dodecyl-N-betaine etc., preferably Triton X-100. If glycolipids are used as the acceptor substrate, the surfactant is added in a suitable amount to the reaction solution so that they can be reacted sufficiently. In this reaction, both the acceptor substrate and donor substrate are preferably contained preferably at a 5-fold or 10-fold or more concentration than Km value (Michaelis constant).

After the reaction was finished, the resulting reaction product (sialo-derivative corresponding to the acceptor substrate) can be separated and purified by column chromatography etc.

EXAMPLES

The present invention is described in more detail by reference to the following examples, which however are not intended to limit the scope of the present invention.

Production Example 1

Production of β-galactoside-α-2,6-sialyltransferase derived from *Photobacterium damsela* JTO160

A liquid medium Marine Broth 2216 was prepared in a usual manner, pipetted into test tubes (10 ml/tube) and sterilized in an autoclave. *Photobacterium damsela* JTO160 was harvested from colonies previously subcultured in Marine Broth 2216-agar plate (1.5% agar) and was then inoculated into 10 ml of Marine Broth 2216 liquid medium prepared above. The microorganism was pre-cultured at 30° C. for 8 hours with shaking at 150 r.p.m.

The culture thus obtained was further cultured in the following manner. 500 ml Marine Broth 2216 prepared in a usual manner was introduced into 3000 ml flask and sterilized in an autoclave. 5 ml of the above culture was inoculated into the medium and cultured at 30° C. with shaking at 150 r.p.m. for 16 hours. The resulting microorganism was recovered by centrifugation to give a pellet (wet weight: about 2 g).

The microorganism was suspended in 40 ml of 20 mM cacodylate buffer (pH 6.0) containing 1M NaCl and 0.2% Triton X-100 (surfactant available from Kanto Kagaku K.K.) and disrupted by ultrasonication under cooling in ice bath. The disruption was continued until the absorbance at 660 nm of the suspension was below 30%. After the disruption, the bacterial solution was centrifuged at 100,500 g at 4° C. for 1 hour to give a supernatant. The supernatant was introduced into a cellulose tube and dialyzed overnight at 4° C. against 5000 ml of 20 mM cacodylate buffer (pH 6.0) containing 0.2% Triton X-100 as surfactant, during which the buffer was exchanged 3 times with fresh one. After the dialysis, the precipitates occurring in the sample were removed by centrifugation at 100,500 g for 1 hour at 4° C. A crude enzyme solution was thus prepared from the solution of the disrupted microorganism.

The crude enzyme solution was applied to a strong anion exchange column Q-Sepharose HR 26/10 (Pharmacia) previously equilibrated with 20 mM cacodylate buffer (pH 6.0) containing 0.2% Triton X-100 as surfactant. The enzyme was then eluted with a linear gradient of from 20 mM cacodylate buffer (pH 6.0) containing 0.2% Triton X-100 as surfactant to the same buffer containing 1M NaCl (total elution volume: 1060 ml), and fractions with enzyme activity eluted with 0.25 to 0.35M NaCl were recovered and combined.

This enzyme solution was dialyzed overnight at 4° C. against 5000 ml of 20 mM cacodylate buffer (pH 6.0) containing 0.2% Triton X-100 as surfactant, during which the buffer was exchanged 3 times with fresh one. The dialyzate was applied to hydroxyapatite (Koken K.K.) previously equilibrated with 20 mM cacodylate buffer (pH 6.0) containing 0.2% Triton X-100 as surfactant. The sample was eluted with a linear gradient of from 20 mM cacodylate buffer (pH 6.0) containing 0.2% Triton X-100 as surfactant to 0.35M phosphate buffer (pH 6.0) containing 0.2% Triton X-100 as surfactant (total elution volume: 620 ml). Fractions with enzyme activity eluted with 0.08M to 0.16M phosphate buffer were recovered and combined. This enzyme solution was dialyzed overnight at 4° C. against 5000 ml of 20 mM cacodylate buffer (pH 6.0) containing 0.2% Triton X-200 as surfactant, during which the buffer was exchanged 3 times with fresh one.

The dialyzate was applied to Sephacryl S-200 (Pharmacia) i.e. a gel filtration column (2.6×60 cm) and passed through the column with 20 mM cacodylate buffer (pH 6.0) containing 0.1M NaCl and 0.2% Triton X-100 as surfactant, and fractions with enzyme activity, i.e. between 100 ml and 140 ml in elution volume, were recovered and combined. This enzyme solution was dialyzed at 4° C. against 5000 ml of 20 mM cacodylate buffer (pH 6.0) containing 0.2% Triton X-100 as surfactant.

The dialyzate was adsorbed onto a CDP-hexanolamine agarose column (0.7×1.2 cm) previously equilibrated with 20 mM cacodylate buffer (pH 6.0) containing 0.2% Triton X-100 as surfactant, and the column was washed with 4 ml of the same buffer, and the sample was eluted with 8 ml of same buffer containing 2M NaCl. This fraction was dialyzed against 20 mM cacodylate buffer (pH 6.0) containing 0.2% Triton X-100 as surfactant. The SDS-PAGE of this fraction indicated one single band of the enzyme indicating a molecular weight of about 61,000. The specific activity of this fraction was 643-fold higher than that of the solution of the disrupted microorganism. The total activity was 257 U, and 19% of the original activity was recovered.

The activity of the present enzyme was determined by mixing a donor substrate (CMP-sialic acid) and an acceptor substrate (asialoglycoprotein) with an enzyme solution and quantifying the sialic acid transferred during the enzyme reaction to the saccharide-accepting substrate. The detailed procedures for this measurement are as follows:

Asialofetuin was dissolved as the acceptor substrate at a concentration of 6.25 mg/ml in 20 mM cacodylate buffer (pH 6.0), and 80 $\mu$l of the solution was used as the acceptor substrate solution. 10 $\mu$l solution of CMP-sialic acid (6.7 nmol) where sialic acid was labeled with $^{14}$C (6,700 cpm/nmol) was added to the acceptor substrate solution, and the mixture was kept at 30° C. 10 $\mu$l enzyme solution was added to it and reacted for 5 minutes at 30° C. Then, the reaction solution was applied to a column (inner diameter, 10 mm; length, 160 mm) packed with Sephadex G-50 (Pharmacia) previously equilibrated with 0.1M NaCl. The eluent used was 0.1M NaCl. A void-volume fraction containing the acceptor substrate with sialic acid transferred to it by the enzyme reaction was collected and examined for radioactivity. The transferred sialic acid thus determined was used to determine enzyme activity where it was assumed that 1 U of the enzyme is the amount of the enzyme causing transfer of 1 nmol sialic acid per minute.

Example 1

Sialylation of monosaccharides

The enzyme reaction was carried out using the enzyme obtained in Production Example 1 and CMP-sialic acid as the donor substrate. In this reaction, methyl-$\alpha$-D-galactose, methyl-$\beta$-D-galactose, methyl-$\alpha$-D-mannose, methyl-$\beta$-D-mannose, methyl-$\beta$-D-N-acetylglucosamine, and methyl-$\alpha$-D-N-acetylgalactosamine were used respectively as the acceptor substrate. Specifically, 80 mM monosaccharide, 67$\mu$M CMP-sialic acid labeled with a radioisotope (6700 cpm/nmol) and 1 U enzyme were dissolved in 50 $\mu$l of 20 mM cacodylate buffer (pH 6.0) and reacted at 30° C. for 30 minutes.

Figure 1:
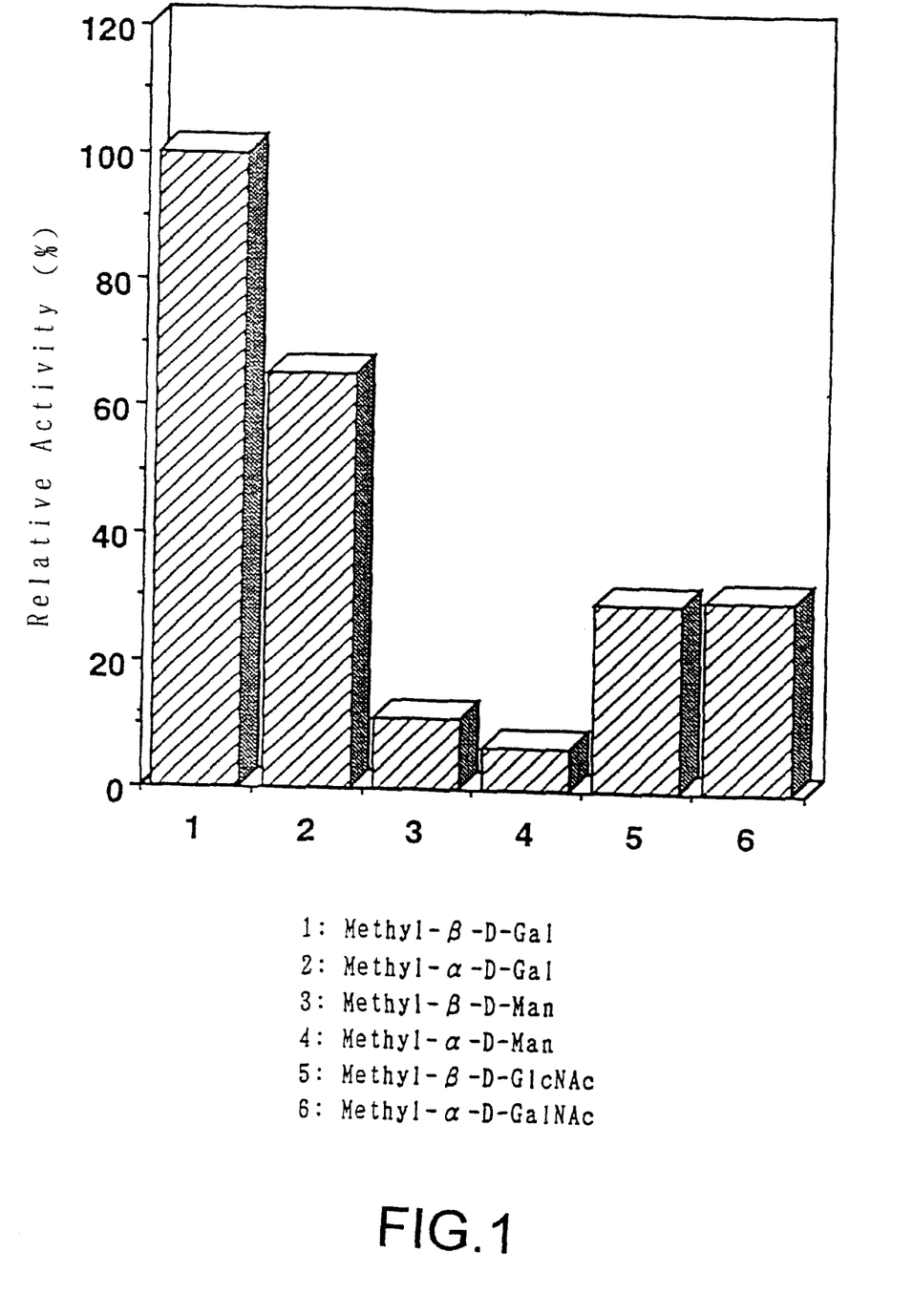
FIG. 1 is a graph showing the relative activity of β-galactoside-α-2,6-sialyltransferase toward each monosaccharide where β-galactoside-α-2,6-sialyltransferase derived from *Photobacterium damsela* JTO160 was used to transfer sialic acid to each monosaccharide.

After the reaction was terminated, the reaction solution was applied to a Dowex 1×2 (phosphate form) column (0.7×2 cm, 0.8 ml resin, manufactured Muromachi Kagaku K.K.) equilibrated with distilled water, and the reaction product was eluted with 5 mM phosphate buffer (pH 6.8). The determined radioactivity of the reaction product indicated that sialic acid was transferred to any of the monosaccharides. The activity of the enzyme towards each acceptor substrate was determined and expressed in percentage relative to the activity (as 100%) towards methyl-$\alpha$-D-galactose. The result is shown in FIG. 1.

Example 2

Production of sialylmethyl-$\beta$-D-N-acetyllactosamine

Sialylmethyl-$\beta$-D-N-acetyllactosamine was produced using methyl-$\beta$-D-N-acetyllactosamine as the acceptor substrate. 79.4 mg (200 $\mu$mol) of methyl-$\beta$-D-N-acetyllactosamine, 9.4 mg (16 $\mu$mol) of CMP-sialic acid, and 270 U of the $\beta$-galactoside-$\alpha$-2,6-sialyltransferase obtained in Production Example 1 were dissolved in 1 ml of 20 mM cacodylate buffer (pH 6.0) and reacted at 30° C. for 1 hour. The progress of the reaction was confirmed on a 1/10 scale under the same conditions by determining sialic acid transferred from CMP-sialic acid labeled with $^{14}$C as the donator substrate. After the reaction was finished, the reaction solution was adjusted to 10 ml with 1 ml distilled water. This solution was applied to a Dowex 1×2 (phosphate form) column (1.5×9 cm, 15.9 ml resin, manufactured by Muromachi Kagaku K.K.) previously equilibrated with distilled water.

The column was washed with 90 ml distilled water and the sample was then eluted with 60 ml of 5 mM sodium phosphate, pH 6.8 and collected (5 ml eluate/fraction). Each fraction was determined for glycoside-linked sialic acid by a periodate-resorcinol method. Fractions containing glycoside-linked sialic acid, eluted between 20 ml and 50 ml in elution volume, were collected and concentrated by a rotary evaporator. This concentrate of the reaction product was applied to an activated-carbon column (1.5×6.8 cm, 12 ml activated carbon, manufactured by Wako Pure Chemical Industries, Ltd.). Then, the column was washed with a 3-fold volume of distilled water relative to the column volume, and the sample was eluted with a 2-fold volume each of 10%, 20%, 50% and 100% ethanol relative to the column volume. Each fraction was determined for glycoside-linked sialic acid by the periodate-resorcinol method. Fractions containing glycoside-linked sialic acid, eluted with 10%, 20% and 50% ethanol, were combined and concentrated by a rotary evaporator.

Figure 2:
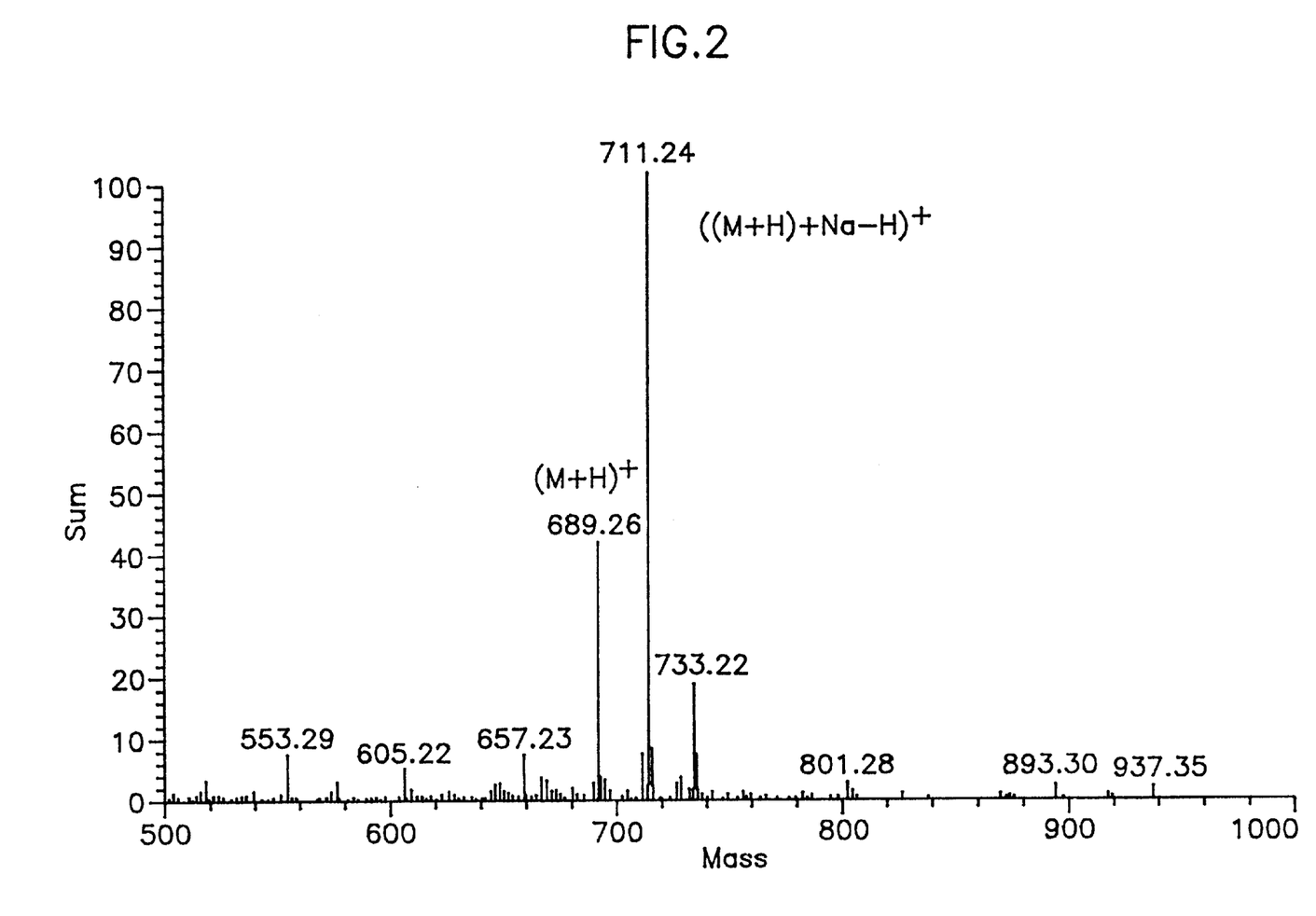
FIG. 2 is a graph showing a mass spectrum of α-2,6-sialylmethyl-β-D-N-acetyllactosamine synthesized by use of β-galactoside-α-2,6-sialyltransferase derived from *Photobacterium damsela* JTO160.

The reaction product was analyzed by mass spectrometry. Its mass spectrum is shown in FIG. 2. The molecular weight of sialylmethyl-β-D-N-acetyllactosamine is 688, and its corresponding peak (molecular weight: 689 (M+H$^+$)) could be seen in the mass spectrum in FIG. 2.

The reaction product was further analyzed by $^1$H-NMR and $^{13}$C-NMR. The results of the $^{13}$C-NMR measurement are shown in Table 1.

TABLE 1

| Sugar Chain | Carbon Atom | Reaction Product | NeuAc$_\alpha$2,6LacNAc (values in literatures) |
|---|---|---|---|
| β-D-GlcNAc | 1 | 102.12 | 102.08 |
|  | 2 | 55.13 | 55.12 |
|  | 3 | 72.84 | 72.83 |
|  | 4 | 81.15 | 81.19 |
|  | 5 | 74.89 | 74.88 |
|  | 6 | 60.77 | 60.79 |
|  | N—C=O | 175.06 | 175.30 |
|  | CH$_3$ | 22.69 | 22.69 |
| β-D-Gal | 1 | 103.87 | 103.86 |
|  | 2 | 71.13 | 71.12 |
|  | 3 | 72.96 | 72.95 |
|  | 4 | 68.80 | 68.77 |
|  | 5 | 74.08 | 74.07 |
|  | 6 | 63.74 | 63.72 |
| α-D-NeuAc(2-6) | 1 | 173.90 | 173.80 |
|  | 2 | 100.57 | 100.54 |
|  | 3 | 40.46 | 40.49 |
|  | 4 | 68.59 | 68.59 |
|  | 5 | 52.31 | 52.30 |
|  | 6 | 72.96 | 72.95 |
|  | 7 | 68.59 | 68.59 |
|  | 8 | 72.10 | 72.09 |
|  | 9 | 63.07 | 63.06 |
|  | N—C=O | 175.35 | 175.61 |
|  | CH$_3$ | 22.43 | 22.42 |

From these results, it became evident that the reaction product formed in the enzyme reaction is α-2,6-sialylmethyl-β-D-N-acetyllactosamine.

From a control experiment using CMP-sialic acid as the donor substrate with sialic acid labeled with $^{14}$C, it was found that 16 μmol of α-2,6-sialylmethyl-β-D-N-acetyllactosamine could be produced under the present conditions.

Example 3

(1) Sialylation of pyridylaminated sugar chains

The enzyme reaction was carried out using the enzyme obtained in Production Example 1 and pyridylaminated sugar chains as the acceptor substrate. The pyridylaminated sugar chains used were N-acetyllactosamine type: biantennary sugar chain (Galβ1-4GlcNAcβ1-2Manα1-6(Galβ1-4GlcNAcβ1-2Manα1-3)Manβ1-4GlcNAc-PA (PA1), produced by Takara Shuzo Co., Ltd.) and 2 kinds of N-acetyllactosamine type monosialylated: biantennary sugar chain (NeuAc α2-6Galβ1-4GlcNAcβ1-2Manα1-6(Galβ1-4GlcNAcβ1-2Manα1-3)Manβ1-4GlcNAcβ1-4GlcNAc-PA (PA2), Galβ1-4GlcNAcβ1-2Manα1-6(NeuAcα2-6Galβ1-4GlcNAcβ1-2Manα1-3)Manβ1-4GlcNAcβ1-4GlcNAc-PA(PA3), produced by Takara Shuzo Co., Ltd.).

The structure of each sugar chain is shown in Table 2.

For any acceptor substrate, 2.0 μM acceptor substrate, 5.7 μM CMP-sialic acid, and 1 U enzyme were dissolved in 25 μl of 20 mM cacodylate buffer (pH 6.0) and the mixture was reacted at 30° C. for 20 hours. After the reaction was finished, the reaction solution was heated at 100° C. for 2 minutes so that the enzyme was inactivated. Then, the reaction product was analyzed in HPLC.

Shimadzu LC-10 (Shimadzu) was used as HPLC system in which Takara PALPAK Type R (Takara Shuzo Co., Ltd.) was used as the column. 10 μl of the reaction solution containing the inactivated enzyme was injected into the column previously equilibrated with 100 mM acetate-triethylamine (pH 5.0) containing 0.15% N-butanol. Using eluent A (100 mM acetate-triethylamine, pH 5.0) and eluent B (100 mM acetate-triethylamine, pH 5.0, containing 0.5% n-butanol), the pyridylaminated sugar chain was eluted in a linear gradient (0 to 35 minutes) of from 30% to 100% eluent B and then with 100% eluent B (35 to 50 minutes) at a flow rate of 1 ml/min. at a column temperature of 40° C. while monitoring the pyridylaminated sugar chain with fluorescence (Ex: 320 nm, Em: 400 nm). In the same manner, the N-acetyllactosamine type disialylated: biantennary sugar chain (NeuAcα2-6Galβ1-4GlcNAcβ1-2Manα1-6(NeuAcα2-6Galβ1-4GlcNAcβ1-2Manα1-3)Manβ1-4GlcNAcβ1-4GlcNAc-PA (PA4)) was eluted and the pyridylaminated sugar chain was detected by its fluorescence. The results are shown in FIG. 3.

Figure 3:
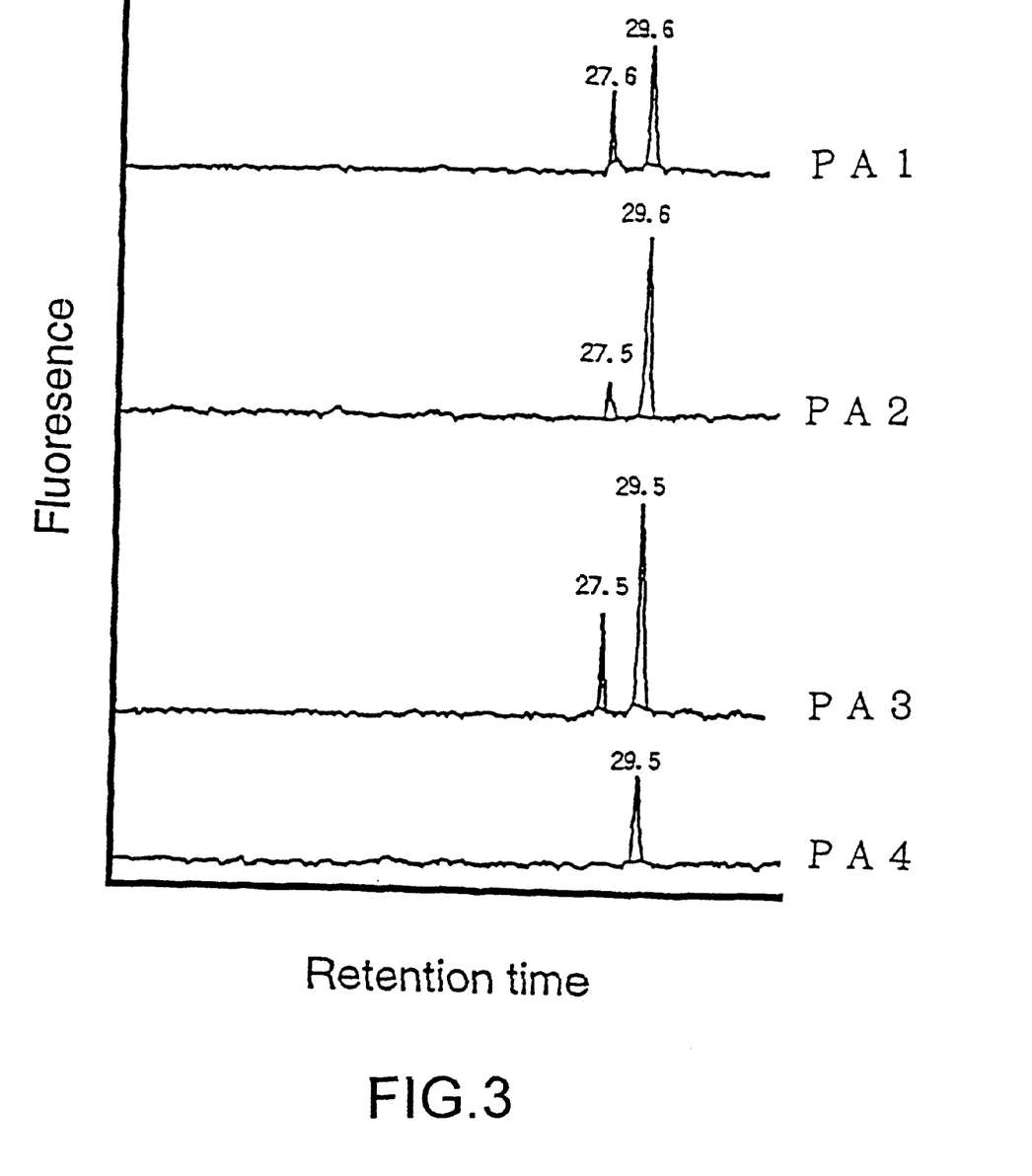
FIG. 3 is a graph showing the result of HPLC analysis of a pyridylaminated sugar chain having sialic acid transferred to it by use of β-galactoside-α-2,6-sialyltransferase derived from *Photobacterium damsela* JTO160.

As is evident from FIG. 3, the same retention time as in PA4 could be detected for PA1 to PA3. From this result, it became evident that the present enzyme could be used to produce N-acetyllactosamine type disialylated: biantennary sugar chain from any of N-acetyllactosamine type: biantennary sugar chain and 2 kinds of N-acetyllactosamine type monosialylated: biantennary sugar chain.

| Sugar Chain No. | Structure |
|---|---|
| PA1 | Galβ1-4GlcNAcβ1-2Manα1-6<br>    Manβ1-4GlcNAcβ1-4GlcNAc-PA<br>Galβ1-4GlcNAcβ1-2Manα1-3 |
| PA2 | NeuAcα2-6Galβ1-4GlcNAcβ1-2Manα1-6<br>    Manβ1-4GlcNAcβ1-4GlcNAc-PA<br>Galβ1-4GlcNAcβ1-2Manα1-3 |
| PA3 | Galβ1-4GlcNAcβ1-2Manα1-6<br>    Manβ1-4GlcNAcβ1-4GlcNAc-PA<br>NeuAcα2-6Galβ1-4GlcNAcβ1-2Manα1-3 |
| PA4 | NeuAcα2-6Galβ1-4GlcNAcβ1-2Manα1-6<br>    Manβ1-4GlcNAcβ1-4GlcNAc-PA<br>NeuAcα2-6Galβ1-4GlcNAcβ1-2Manα1-3 |

Example 4

Sialylation of asialofetuin and asialo-α$_1$-acid glycoprotein

Asialofetuin was dissolved as the acceptor substrate at a concentration of 6.25 mg/ml in 20 mM cacodylate buffer (pH 6.0), and 80 μl of the solution was used as the acceptor substrate solution. 10 μl solution of CMP-sialic acid (6.7 nmol) with sialic acid labeled with $^{14}$C (6,700 cpm/nmol) was added to the acceptor substrate solution, and the mixture was kept at 30° C. 10 μl of the crude enzyme solution obtained in Production Example 1 was added to it and reacted for 5 minutes at 30° C. Then, the reaction solution was applied to a column (inner diameter, 10 mm; length, 160 mm) packed with Sephadex G-50 (Pharmacia) previously equilibrated with 0.1M NaCl. The eluent used was 0.1M NaCl. A high-molecular, void-volume fraction containing asialofetuin with sialic acid transferred to it by the enzyme reaction was collected and examined for radioactivity. The result indicated that the radioactivity was 3125 cpm on average.

As the control, a solution was prepared by adding 10 μl of 20 mM cacodylate buffer (pH 6.0) in place of the enzyme solution to a mixture of 80 μl acceptor substrate solution and 10 μl of CMP-sialic acid (labeled with $^{14}C$) (6.7 nmol, 6,7000 cpm/nmol). This control solution was incubated at 30° C. for 5 minutes and then applied to the same gel filtration column as above, and the radioactivity of the void-volume fraction was determined in the same manner as above. The result indicated that the radioactivity was 30 cpm on average.

This radioactivity of the void-volume fraction in the control was subtracted from the above radioactivity of the void-volume fraction from the sample subjected to the enzyme reaction, whereby the sialic acid transferred by the enzyme was determined. This result showed that 3 nmol sialic acid was transferred to asialofetuin under the above conditions.

Similarly, asialo-$\alpha_1$-acid glycoprotein was used as the acceptor solution and the same enzyme reaction as above was carried out. The result indicated that the radioactivity of the void-volume fraction was 2985 cpm on average, while the radioactivity of the void-volume fraction from the control was 35 cpm on average. This result showed that 2.9 nmol sialic acid was transferred to asialo-$\alpha_1$-acid glycoprotein under the above conditions.

Production Example 2

Production of β-galactoside-α-2,6-sialyltransferase derived from *Photobacterium damsela* ATCC 33539 and ATCC 35083

ATCC 33539 and ATCC 35083 were cultured respectively in a liquid medium Marine Broth 2216 (Difco). After the microorganisms were sufficiently grown, they were harvested from each of the cultures by centrifugation. The microorganisms were suspended in 20 mM cacodylate buffer (pH 6.0) containing 0.2% Triton X-100 (Kanto Kagaku K.K.) as surfactant. The cells were disrupted by ultrasonication of the suspension under cooling in ice bath to give crude enzyme solutions.

Example 5

(2) Sialylation of a pyridylaminated sugar chain

The enzyme reaction was carried out with a pyridylaminated sugar chain as the acceptor substrate using each of the enzymes obtained in Production Example 2. Pyridylaminated lactose (Galβ1-4Glc-PA, produced by Takara Shuzo Co., Ltd.) was used as the pyridylaminated sugar chain and analyzed in the same manner as in Example 3.

Figure 4:
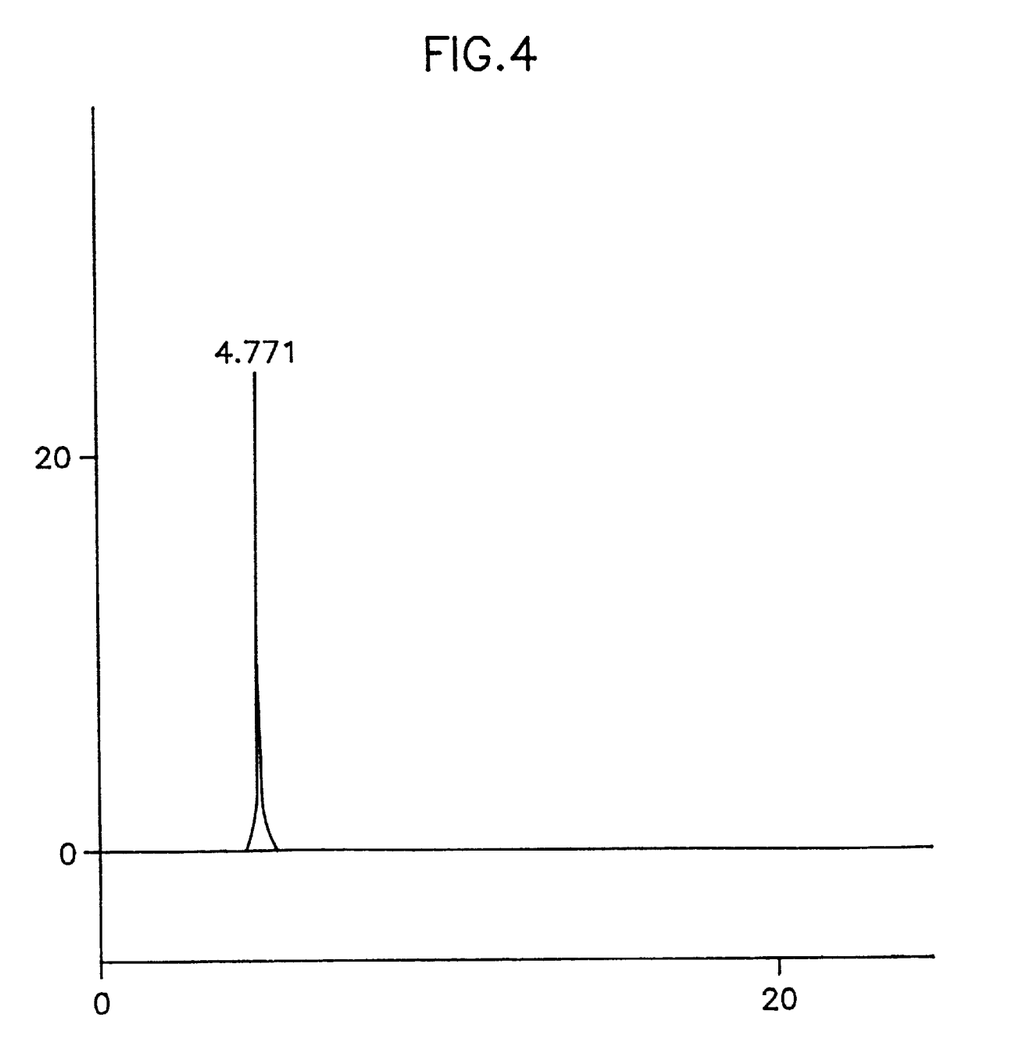
FIG. 4 is a graph showing the result of HPLC analysis of pyridylaminated lactose.
Figure 5:
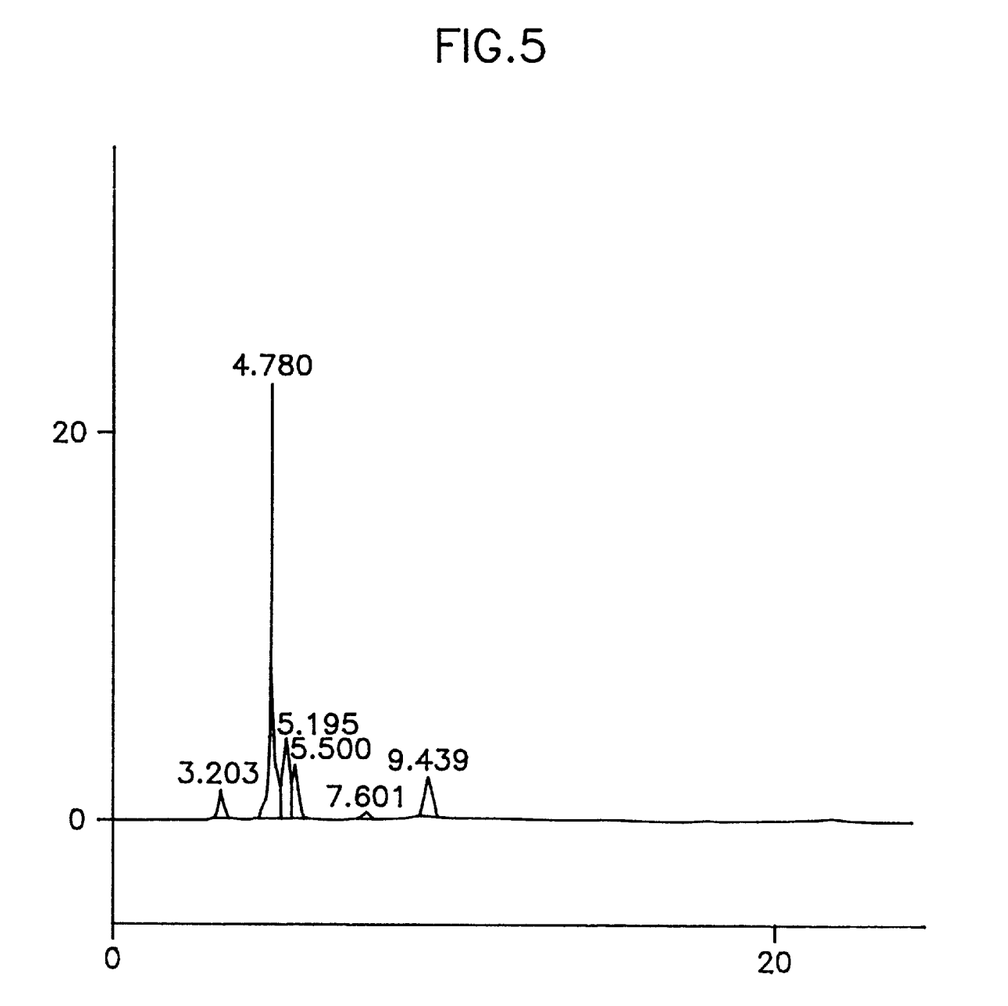
FIG. 5 is a graph showing the result of HPLC analysis of pyridylaminated α-2,6-sialyllactose synthesized by use of β-galactoside-α-2,6-sialyltransferase derived from *Photobacterium damsela* ATCC 33539.

FIG. 4 shows the result of HPLC analysis of the acceptor substrate; FIG. 5 shows the result of HPLC analysis of the reaction product using the enzyme derived from ATCC 33539; and FIG. 6 shows the result of HPLC analysis of the reaction product using the enzyme derived from ATCC 35083.

Figure 6:
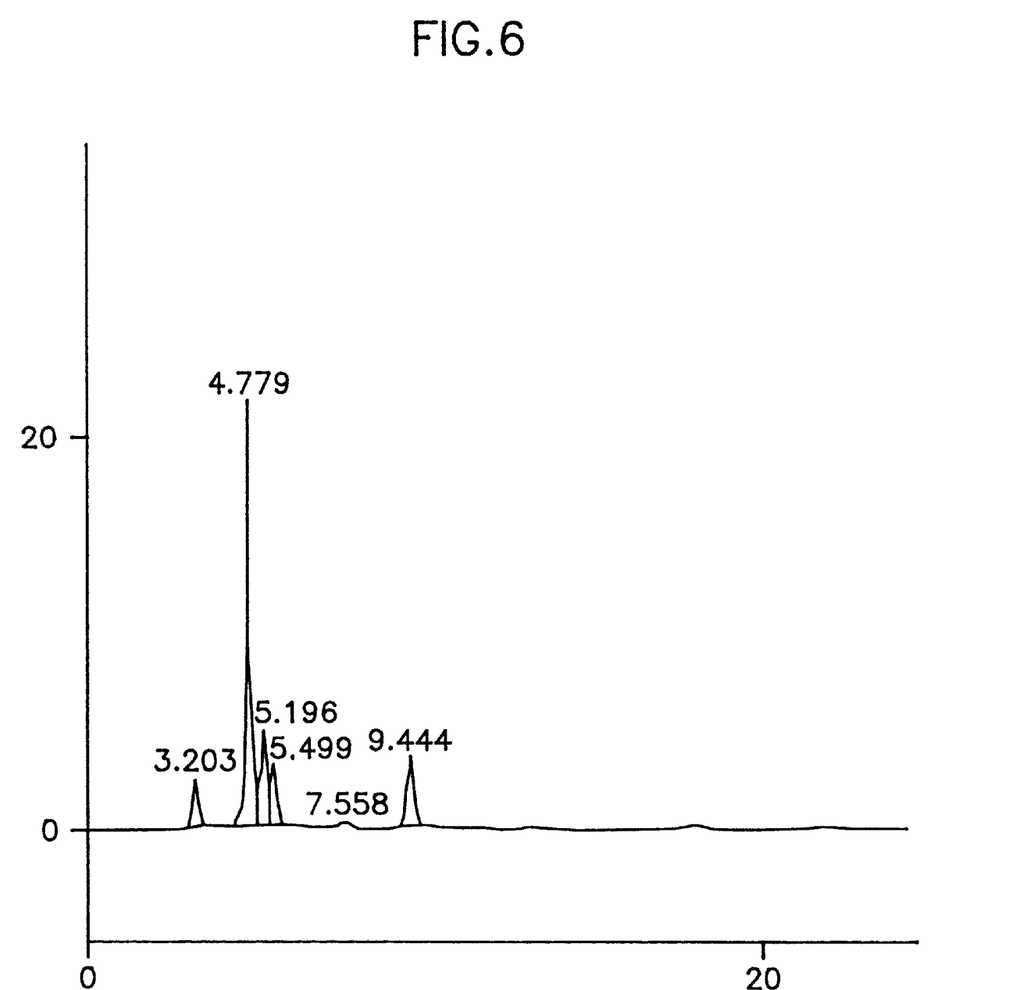
FIG. 6 is a graph showing the result of HPLC analysis of pyridylaminated α-2,6-sialyllactose synthesized by use of β-galactoside-α-2,6-sialyltransferase derived from *Photobacterium damsela* ATCC 35083.

In FIG. 5, the peak with a retention time of 5.500 indicates pyridylaminated α2,6-sialyllactose, and in FIG. 6, the peak with a retention time of 5.499 indicates pyridylaminated α2,6-sialyllactose.

These result showed that the present enzyme can be used to produce pyridylaminated α-2,6-sialyllactose from pyridylaminated lactose.

Effect of the Invention

According to the present invention, there is provided a method of producing saccharides containing sialic acid. According to the present invention, saccharides containing sialic acid can be produced easily and inexpensively.

---

---

What is claimed is:

1. A method of production of saccharides containing sialic acid, comprising the step of:

contacting β-galactoside-α-2,6-sialyltransferase derived from a microorganism belonging to the genus Photobacterium with a glycoconjugate having a sugar chain containing a galactose residue, a free sugar chain having a galactose residue or a monosaccharide having a hydroxyl on a carbon atom at 6-position under conditions which allow linking of sialic acid to said 6-position of said galactose residue in a sugar chain of said glycoconjugate or the 6-position of said galactose residue in said free sugar chain, or to said 6-position of said monosaccharide having a hydroxyl group on carbon at said 6-position and being capable of forming an oligosaccharide or a glycoconjugate.

2. The method according to claim 1, wherein β-galactoside-α-2,6-sialyltransferase has the following physicochemical properties:

(a) action and specificity: (i) transferring sialic acid from cytidine monophosphate-sialic acid to the 6-position of a galactose residue in a sugar chain of a glycoconjugate or in a free sugar chain, or to the 6-position of a monosaccharide having a hydroxyl group on carbon at the 6-position and (ii) being capable of forming an oligosaccharide or a glycoconjugate;

(b) optimum pH: 5 to 6;

(c) optimum temperature: 30° C.; and (d) molecular weight: 64,000±5,000 (determined by gel filtration).

3. The method according to claim 1, wherein β-galactoside-α2,6-sialyltransferase has the following physicochemical properties:

(a) action and specificity: (i) transferring sialic acid from cytidine monophosphate-sialic acid to the 6-position of a galactose residue in a sugar chain of a glycoconjugate or in a free sugar chain, or to the 6-position of a monosaccharide having a hydroxyl group on carbon at the 6-position and (ii) being capable of forming an oligosaccharide or a glycoconjugate;

(b) optimum pH: 5;

(c) optimum temperature: 30° C.;

(d) pH stability: 4.5 to 6;

(e) thermal stability: keeping about 90% of the initial activity after heating at 35° C. for 5 minutes and about 70% of the initial activity after heating at 45° C. for 5 minutes;

(f) molecular weight: about 61,000 (determined by 12.5% SDS-polyacrylamide gel electrophoresis) and about 64,000 (determined by gel filtration);

(g) N-terminal amino acid sequence:
X-Asn-Ser-Asp-Asn-Thr-Ser-Leu-Lys-Glu-Thr-Val (SEQ ID NO: 1); and (h) isoelectric point: 4.6.

4. The method of claim 1, wherein said β-galactoside-α-2,6-sialyltransferase is present in crude enzyme solution.

5. The method according to claim 1, wherein said Photobacterium is *Photobacterium damsela* deposited as Ferm BP-6135.

6. The method according to claim 1, wherein said Photobacterium is *Photobacterium damsela* deposited as Ferm BP-6136.

7. The method according to claim 1, wherein said Photobacterium is *Photobacterium damsela* deposited as Ferm BP-4900.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: Not Relevant
      (D) TOPOLOGY: linear    (ii) MOLECULE TYPE: peptide    (xi) SEQUENCE DESCRIPTION: SEQ ID NO:1:

Xaa Asn Ser Asp Asn Thr Ser Leu Lys Glu Thr Val
   1             5                 10